(12) United States Patent
Mueller et al.

(10) Patent No.: US 10,758,656 B2
(45) Date of Patent: Sep. 1, 2020

(54) DIALYSIS MACHINE AND A METHOD FOR OPERATING A PNEUMATIC SYSTEM OF A DIALYSIS MACHINE

(71) Applicant: FRESENIUS MEDICAL CARE DEUTSCHLAND GMBH, Bad Homburg (DE)

(72) Inventors: Ralf Mueller, Bad Homburg (DE); Soeren Gronau, Ruesselsheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 494 days.

(21) Appl. No.: 15/568,345

(22) PCT Filed: Apr. 20, 2016

(86) PCT No.: PCT/EP2016/000642
§ 371 (c)(1),
(2) Date: Apr. 13, 2018

(87) PCT Pub. No.: WO2016/169651
PCT Pub. Date: Oct. 27, 2016

(65) Prior Publication Data
US 2018/0214622 A1    Aug. 2, 2018

(30) Foreign Application Priority Data

Apr. 22, 2015  (DE) .................. 10 2015 005 179

(51) Int. Cl.
| | | |
|---|---|---|
| *A61M 1/16* | (2006.01) | |
| *A61M 1/14* | (2006.01) | |
| *A61M 1/36* | (2006.01) | |

(52) U.S. Cl.
CPC ............ *A61M 1/1658* (2013.01); *A61M 1/14* (2013.01); *A61M 1/3635* (2014.02); *A61M 2205/3331* (2013.01); *A61M 2205/3337* (2013.01)

(58) Field of Classification Search
CPC .............. A61M 1/1656; A61M 1/1658; A61M 1/3635; A61M 1/14; A61M 1/1635;
(Continued)

(56) References Cited

U.S. PATENT DOCUMENTS

| | | | | |
|---|---|---|---|---|
| 4,348,280 A | * | 9/1982 | George ............... | A61M 1/1656 210/101 |
| 4,381,999 A | * | 5/1983 | Boucher ............. | A61M 1/1656 210/637 |

(Continued)

FOREIGN PATENT DOCUMENTS

WO    WO 2014/090746    6/2014

*Primary Examiner* — Philip R Wiest
(74) *Attorney, Agent, or Firm* — Jacobson Holman, PLLC.

(57) ABSTRACT

The present invention relates to a dialysis machine having a hydraulic system that is intended for providing a dialysis solution or an element of the dialysis solution, wherein the hydraulic system has a degassing pump for degassing the dialysis solution or an element of the dialysis solution, and having a pneumatic system in which a vacuum is present at least at times for operating a component of the dialysis machine, wherein there is a connection line between the suction side of the degassing pump and the pneumatic system for a vacuum generation in the pneumatic system.

15 Claims, 1 Drawing Sheet

(58) Field of Classification Search
CPC ........ A61M 1/1649; A61M 2250/3331; A61M 2250/3337
See application file for complete search history.

(56) References Cited

U.S. PATENT DOCUMENTS

| | | | |
|---|---|---|---|
| 2010/0106071 A1* | 4/2010 | Wallenborg | A61M 1/1658 604/5.01 |
| 2011/0120302 A1* | 5/2011 | Raiford | A61M 1/167 95/19 |
| 2012/0265117 A1* | 10/2012 | Fava | A61M 1/3646 604/6.09 |
| 2013/0025692 A1* | 1/2013 | Heide | A61M 1/16 137/1 |
| 2013/0028788 A1 | 1/2013 | Gronau et al. | |
| 2014/0174542 A1* | 6/2014 | Jansson | A61M 1/3621 137/1 |
| 2018/0036470 A1* | 2/2018 | Hasegawa | A61M 1/301 |

* cited by examiner

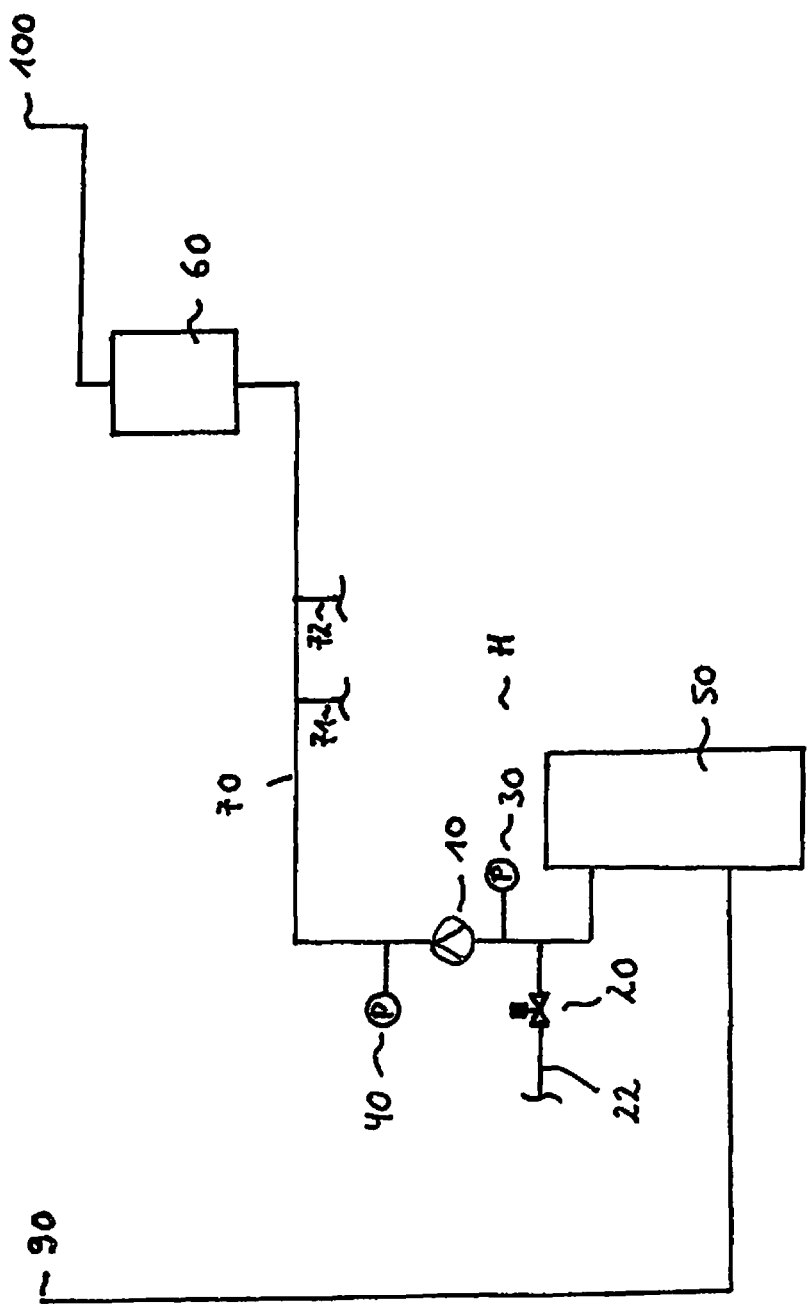

ND A METHOD FOR
DIALYSIS MACHINE AND A METHOD FOR OPERATING A PNEUMATIC SYSTEM OF A DIALYSIS MACHINE

The present invention relates to a dialysis machine having a hydraulic system that is intended for providing the dialysis solution or an element of the dialysis solution, wherein the hydraulic system has a degassing pump for degassing the dialysis solution or the element of the dialysis solution, and having a pneumatic system in which a vacuum is present at least at times for operating a component of the dialysis machine.

A hydraulic system is provided in dialysis machines known from the prior art that, for example, has lines, valves, pumps, etc. This hydraulic system is typically connected to a water inlet and serves to convey and degas the water serving the preparation of the dialysis solution or that serves to prepare the finished dialysis solution.

A degassing pump is provided for the degassing that typically generates a vacuum in a degassing container, i.e. the degassing container is at the suction side of the degassing pump.

Gas is separated from the water or from another fluid by the vacuum generation in the degassing container and is led off. The water degassed in this manner can be conveyed by means of the degassing pump into a mixing system, for example, for preparing the dialysis solution with further components or concentrates or can also be conveyed into a balancing chamber system of the dialysis machine.

Known dialysis machines furthermore have a pneumatic system in which a vacuum is present at least at times. The vacuum is generated by a compressor of the pneumatic system. Actuators such as pistons and cylinders are operated with compressed air and vacuum. It is also possible to utilize the generated vacuum e.g. to support a pressure measurement.

The demands on leak tightness are frequently greater and are simultaneously more complex to implement in a vacuum than in excess pressure systems. Said pneumatic system thus has to be manufactured in a correspondingly complex manner or with complex and/or expensive components to be able to implement sufficient leak tightness and thus a reliable maintenance of the vacuum.

The noise generated by compressor of the pneumatic system that is running or is starting up plays a role in dialysis machines having such a pneumatic system in that the patients and the clinical staff are typically exposed to these noises simultaneously from a plurality of devices.

Against this background, the aim is to keep the running times and the number of start-up cycles of the compressor as small as possible, which, however, requires that the demand on leak tightness is correspondingly further increased for the total vacuum system of the pneumatic system, which is cost-intensive.

The running times and the number of start-up cycles of the compressor also play an essential role with respect to the service life of the compressor and thus also with respect to the costs for the compressor component to be selected.

It is thus advantageous to keep the running times and start-up cycles of the compressor as small as possible due to aspects of cost and noise. A further demand is that the leak tightness of the pneumatic system at all leak tight points is not increased beyond the degree that is achievable without special measures such as the selection of pneumatic assembly parts. This has a direct influence on the component costs and, via the service life also via the availability, as well as on the repair costs.

It is thus the underlying object of the present invention to further develop a dialysis machine of the initially named kind such that a vacuum production is possible in the pneumatic system with a small cost and noise effort.

This object is satisfied by a dialysis machine having the features of claim 1. Provision is accordingly made that there is at least one connection line between the suction side of the degassing pump and the pneumatic system for vacuum generation in the pneumatic system.

It is possible by this connection line that is connected to the suction side of the degassing pump of the hydraulic system to achieve a vacuum generation in the pneumatic system without a separate compressor in the pneumatic system being required for this purpose.

The term "suction side of the degassing pump" is to be understood broadly and does not, for example, only comprise the line leading to the pump, but also other components that are connected to the suction side of the degassing pump such as the degassing container etc.

The vacuum generation that is available over the total treatment time, but at least during the operating time of the degassing pump of the hydraulic system, can thus be provided by means of a pump (degassing pump) that is anyway running or is anyway present. Additional noise does not thereby arise and the vacuum is also available to a sufficient degree with an increased leakage.

The comfort of such a dialysis machine is thus increased overall since the compressor noise can be omitted. The costs of the dialysis machine are lowered, with a simultaneous increase in availability, by the use of standard components.

Provision is preferably made that the connection line is controllable, which is to be understood such that at least one valve or another cut-off element is located in the connection line and the connection line can be opened and closed as well as optionally also restricted by means of it.

If there is no need for a further vacuum generation in the pneumatic system, the valve can be or remain closed; if, however a vacuum generation should take place, the valve is preferably opened with a running degassing pump so that a vacuum generation takes place in the pneumatic system by means of the degassing pump.

It is conceivable that a pressure sensor is located in the pneumatic system and that the dialysis machine has a control or regulation unit that is configured such that it actuates the degassing pump and/or the valve located in the connection line in dependence on the measured pressure value. It is thus possible to maintain the pressure in the pneumatic system at a desired value or at least within a desired range.

Provision is preferably made that the pneumatic system, unlike known dialysis machines, has no compressor for generating a vacuum in the pneumatic system. This brings about advantages with respect to the costs, the servicing intensity and also the background noise of the dialysis machine.

In this case, the vacuum in the pneumatic system is only generated by the degassing pump of the hydraulic system. However, embodiments are also generally covered by the invention in which the pneumatic system has such a compressor to assist the vacuum generation.

The component to be actuated by the vacuum can, for example, be any desired actuator such as a piston or a cylinder. It is also conceivable that the vacuum in the pneumatic system is used to assist a pressure measurement. Said piston or cylinder can be actuated to control flows within a cassette for the dialysis solution or also flows through a line system, e.g. for the dialysis solution or for inflowing water, etc.

It is conceivable that the hydraulic system has at least one degassing chamber and that a pressure gauge is provided to measure the pressure in the degassing chamber. The dialysis machine can have a control or regulation unit that is configured such that it controls the valve in dependence on the measured pressure.

As initially stated, provision is preferably made that fresh water or RO water that is required to prepare the dialysis solution is conducted into a degassing chamber. A vacuum is generated in the degassing chamber by the degassing pump, whereby a degassing of the water takes place. The gaseous portion is drawn off and the liquid portion is conveyed by means of the degassing e.g. into a mixing chamber or also into a balancing chamber system of the dialysis machine. The mixing chamber can be configured such that the degassed water is e.g. mixed with a concentrate to prepare the finished dialysis solution.

If the valve is controlled or regulated in dependence on the measured pressure in the degassing chamber, it can thereby be achieved that the pressure in the degassing chamber is not influenced too much or does not fall below a limit value. It can thus be prevented that the pressure in the degassing chamber falls below a lower limit value and it can be ensured that the pressure in the degassing chamber remains within a specific desired value range to reliably ensure the degassing of the water.

It is thus conceivable that the opening time of the valve is limited so that the pressure in the degassing chamber is not influenced too much or is not lowered too much.

Provision is made in an embodiment of the invention that the dialysis machine has a balancing chamber system for balancing the fluid volume supplied to a dialyzer of the dialysis machine and led off therefrom. This balancing chamber system, for example, serves the control or setting of the ultrafiltration volume or the ultrafiltration rate. The dialysis machine can furthermore have a control or regulation unit that is configured such that is controls the valve in the at least one connection line in dependence on the degree of filling of the balancing chamber system.

It is thus conceivable that a vacuum generation only takes place in the pneumatic system when the balancing chamber is completely filled. For this purpose, the state of the balancing chamber is evaluated and the valve is kept closed during the filling phase. Once the balancing chamber is filled, the valve can be opened as required by a vacuum in the pneumatic system.

Provision is made as a further embodiment of the invention that the pump capacity, for example the speed of the degassing pump, is variable.

It is thus possible that the dialysis machine has a control or regulation unit that is configured such that it controls or regulates the pump capacity of the degassing pump in dependence on the valve position.

It is thus conceivable that the speed of the degassing pump or its capacity is increased during the phases of the vacuum generation in the pneumatic system to accelerate the vacuum generation in the pneumatic system, on the one hand, and not to influence or lower the pressure in the degassing chamber too much, on the other hand.

If the valve is thus opened to generate vacuum in the pneumatic system, provision can be made that the delivery rate of the degassing pump is increased for this time period for which the valve is open. The valve can be briefly opened as a further option. It can opened and closed at intervals to generate a vacuum in the pneumatic system or to maintain a specific vacuum value or range.

The present invention furthermore relates to a method of operating a pneumatic system of a dialysis machine in accordance with the invention, wherein the method comprises the step that the vacuum in the pneumatic system is generated only or by or also by the degassing pump of the hydraulic system of the dialysis machine.

Provision is preferably made that the vacuum is only generated by the degassing pump of the hydraulic system so that a vacuum generation means, in particular a compressor for the pneumatic system, can be dispensed with.

As stated above, the connection line between the suction side of the degassing pump and the pneumatic system can be opened or closed as required by a valve.

It is conceivable that the dialysis machine has a balancing chamber system and that the valve remains closed during the filling phase of the balancing chamber system.

Provision can be made alternatively or additionally thereto that the dialysis machine has a degassing chamber that is arranged at the suction side of the degassing pump and that the valve is opened or closed in dependence on the pressure present in the degassing chamber. It is possible in this manner to maintain a specific pressure value or a specific pressure range in the degassing chamber or to prevent the pressure in the degassing chamber from falling below a lower limit value.

The pump capacity of the degassing pump can be increased during the phases of the vacuum generation in the pneumatic system. It is thereby possible to prevent the pressure dropping too much in the degassing chamber and simultaneously a fast vacuum generation in the pneumatic system is thereby achieved.

In an option, the valve can be briefly opened. A valve closing and opening at intervals is conceivable to achieve the vacuum generation in the pneumatic system.

Due to the fact that the vacuum generation is already present due to the anyway present degassing pump, the frequency and duration of the pressure build-up phases play a subordinate role and the demands on the inner leak tightness of the pneumatic valves or other elements of the pneumatic system can be reduced. The vacuum reservoir can also be reduced in size, which makes further savings possible.

Further details and advantages of the invention will be explained in more detail with reference to an embodiment shown in the drawing.

The only FIGURE shows a part of the hydraulic system of a dialysis machine in accordance with the invention in a schematic representation.

Reference numeral 90 marks a water inflow of the hydraulic system of a dialysis machine marked by the reference symbol H.

The water is required to prepare a dialysis solution therefrom that is supplied to the balancing chamber system 60. Reference numeral 100 marks the connector via which the completed dialysis solution is supplied to a dialyzer, not shown, of the dialysis machine.

The dialyzer has two chambers that are separated from one another by one or more semipermeable membranes, preferably in the form of a plurality of hollow fibers that have semipermeable walls. The dialyzate chamber is flowed through by the prepared dialysis solution and the blood chamber is flowed through by the blood of the patient that flows through an extracorporeal circuit.

The inflowing water 90 enters into the degassing container 50 in which a vacuum is generated by means of the degassing pump 10.

The degassing pump 10 conveys the degassed water into the line 70. Concentrates that are mixed with the water to prepare the completed dialysis solution in this manner are admixed via inflow lines 71, 72 there. Said dialysis solution is then supplied to the balancing chamber system 60 and is supplied from there to the dialyzate side of the dialyzer.

As can further be seen from the FIGURE, the connection line 22 in which a cut-off valve 20 is located extends from the suction side or from the inflow of the degassing pump 10 at the suction side. The cut-off valve has a drive unit by means of which the valve can be opened and closed.

The line 22 extends to a pneumatic system, not shown in the FIGURE, of the dialysis machine in which pneumatic system a vacuum is present. Reference numerals 30 and 40 mark sensors for measuring the pressure before and after the degassing pump 10. These sensors 30, 40 are not necessarily components of the dialysis machine, but rather serve in the embodiment shown here the checking of the pressure conditions in a pressure maintenance test or in the preparation of the dialysis solution.

If a vacuum is required in the pneumatic system, the valve 20 is opened, preferably with a running degassing pump 10, and the vacuum is thus also generated in the pneumatic system by the degassing pump 10.

An additional compressor separately provided for the vacuum generation is not provided in the pneumatic system. Advantages with respect to noise, cost and servicing thereby result.

Trials have shown that the vacuum generation capacity of the degassing pump 10 is sufficient to maintain a sufficient vacuum in the pneumatic system during the preparation of the dialysis treatment.

The vacuum branch of the pneumatic system was connected to the hydraulic system H of the dialysis machine via the line 22 with an open valve 20. During the preparation phase of the dialysis treatment, the generated vacuum never increased beyond a specific limit value, i.e. a desired vacuum level was always able to be maintained during the preparation of the treatment.

It was able to be shown in a pressure maintenance test that a sufficient vacuum can be generated by the hydraulic system or by the degassing pump 10 in the pneumatic system. A sufficient vacuum level was thus able to be achieved in the pneumatic system with a constant speed of the degassing pump in a relatively short time that allows, for example, actuators, etc. to be actuated.

It was able to be shown by an increase of the vacuum generation capacity by the increase in the speed of the degassing pump 10 that a sufficiently high vacuum was able to be achieved in the pneumatic system within an even shorter time.

As already stated above, it is not absolutely necessary that the connection line 22 is connected to the line of the pump 10 at the suction side. It is also conceivable that the connection line, for example, opens into the degassing container 50 in which a vacuum is present.

The connection line can be connected directly or also indirectly to the suction side of the degassing pump.

It is possible by the present invention to provide a dialysis machine that allows a sufficient vacuum to be provided in the pneumatic system with a comparatively small cost effort, service effort and with less background noise during the preparation and carrying out of a dialysis treatment.

The invention claimed is:

1. A dialysis machine having a hydraulic system that is intended for providing a dialysis solution or an element of the dialysis solution, wherein the hydraulic system has a degassing pump for degassing the dialysis solution or an element of the dialysis solution, and having a pneumatic system in which a vacuum is present at least at times for operating a component of the dialysis machine,
characterized in that there is a connection line between the suction side of the degassing pump and the pneumatic system for vacuum generation in the pneumatic system.

2. A dialysis machine in accordance with claim 1, characterized in that a valve by which the connection line can be opened and closed is present in the connection line.

3. A dialysis machine in accordance with claim 1, characterized in that there is a pressure sensor in the pneumatic system; and in that the dialysis machine has a control or regulation unit that is configured such that it actuates the degassing pump and/or the valve located in the connection line in dependence on the value measured by the pressure sensor.

4. A dialysis machine in accordance with claim 1, characterized in that the pneumatic system does not have a compressor for generating a vacuum in the pneumatic system.

5. A dialysis machine in accordance with claim 1, characterized in that the component to be actuated by the vacuum is an actuator, in particular a piston or a cylinder.

6. A dialysis machine in accordance with claim 2, characterized in that the hydraulic system has a degassing chamber; and in that a pressure gauge for measuring the pressure in the degassing chamber is provided; and in that the dialysis machine has a control or regulation unit that is configured such that it controls the valve in dependence on the measured pressure.

7. A dialysis machine in accordance with claim 2, characterized in that the dialysis machine has a balancing chamber for balancing the fluid volume supplied to a dialyzer and led off therefrom; and in that the dialysis machine has a control or regulation unit that is configured such that it controls the valve in dependence on the degree of filling of the balancing chamber system.

8. A dialysis machine in accordance with claim 2, characterized in that the pump capacity of the degassing pump is variable.

9. A dialysis machine in accordance with claim 8, characterized in that the dialysis machine has a control or regulation unit that is configured such that it controls or regulates the pump capacity of the degassing pump in dependence on the valve position.

10. A dialysis machine in accordance with claim 2, characterized in that the dialysis machine has a control or regulation unit that is configured such that it opens and closes the valve for building up the vacuum in the pneumatic system at intervals.

11. A method of operating a pneumatic system of a dialysis machine in accordance with claim 1, wherein the vacuum in the pneumatic system is generated only or also by the degassing pump of the hydraulic system of the dialysis machine.

12. A method in accordance with claim 11, characterized in that the connection line between the suction side of the degassing pump and the pneumatic system is closed or opened by a valve as required.

13. A method in accordance with claim 12, characterized in that the dialysis machine has a balancing chamber system; and in that the valve remains closed during the filling phase of the balancing chamber system; and/or in that the dialysis machine has a degassing chamber; and in that the valve is opened or closed in dependence on the pressure present in the degassing chamber.

14. A method in accordance with claim 11, characterized in that the pump capacity of the degassing pump is increased during the phases of vacuum generation in the pneumatic system.

15. A method in accordance with claim 12, characterized in that the valve is closed and opened at intervals in the degassing line.

* * * * *